(12) United States Patent
Siccardi et al.

(10) Patent No.: US 10,987,233 B2
(45) Date of Patent: Apr. 27, 2021

(54) DEVICE AND KIT FOR POSITIONING AN IMPLANT FOR INTERVERTEBRAL FUSION

(71) Applicant: MEDACTA INTERNATIONAL S.A., Castel San Pietro (CH)

(72) Inventors: Francesco Siccardi, Castel San Pietro (CH); Meinrad Fiechter, Castel San Pietro (CH); Peter Petrie, Castel San Pietro (CH); Marco Riva, Castel San Pietro (CH)

(73) Assignee: MEDACTA INTERNATIONAL S.A., Castel San Pietro (CH)

( * ) Notice: Subject to any disclaimer, the term of this patent is extended or adjusted under 35 U.S.C. 154(b) by 187 days.

(21) Appl. No.: 16/310,244

(22) PCT Filed: Jun. 6, 2017

(86) PCT No.: PCT/IB2017/053317
§ 371 (c)(1),
(2) Date: Dec. 14, 2018

(87) PCT Pub. No.: WO2017/216676
PCT Pub. Date: Dec. 21, 2017

(65) Prior Publication Data
US 2019/0328545 A1 Oct. 31, 2019

(30) Foreign Application Priority Data
Jun. 15, 2016 (IT) .......................... 102016000006177

(51) Int. Cl.
*A61F 2/46* (2006.01)
(52) U.S. Cl.
CPC .......... *A61F 2/4611* (2013.01); *A61F 2/4603* (2013.01); *A61F 2002/4622* (2013.01); *A61F 2002/4628* (2013.01)

(58) Field of Classification Search
CPC .................................................... A61F 2/4611
See application file for complete search history.

(56) References Cited

U.S. PATENT DOCUMENTS 6,319,257 B1 * 11/2001 Carignan .............. A61F 2/4601
606/205
8,579,904 B2 11/2013 Siccardi
(Continued)

FOREIGN PATENT DOCUMENTS

WO    2011056172 A1    5/2011

OTHER PUBLICATIONS

International Search Report for PCT/IB2017/053317, dated Sep. 21, 2017, 3 pages.

*Primary Examiner* — Andrew Yang
(74) *Attorney, Agent, or Firm* — Meunier Carlin & Curfman LLC

(57) ABSTRACT

A device for positioning an implant for intervertebral fusion, comprising: a handle; a rod protruding from the handle along a main direction of extension of the device up to a free end; a coupler which couples with an implant for intervertebral fusion operatively active at the free end; wherein said coupler comprises: an axial retention assembly provided with a gripper arranged at said free end of the rod and selectively operable between a clamping and a releasing configuration, and an anti-rotational constraint assembly selectively movable between a locking position, in which it is arranged around said axial retention assembly and abuts said implant to prevent its rotation, and a disengagement position, in which it leaves the implant free to rotate in the gripper; and wherein the axial retention assembly and the anti-rotational constraint assembly are structurally different and complementary.

18 Claims, 6 Drawing Sheets

(56) References Cited

U.S. PATENT DOCUMENTS

2006/0235426 A1 10/2006 Roy et al.
2015/0025639 A1* 1/2015 Lindenmann ......... A61F 2/4684
623/17.16

* cited by examiner

DEVICE AND KIT FOR POSITIONING AN IMPLANT FOR INTERVERTEBRAL FUSION

The present application is a National Phase Entry of PCT International Application No. PCT/IB2017/053317, which was filed on Jun. 6, 2017, and which claims priority to Application No. 10/2016000061771 filed in Italy on Jun. 15, 2016, the contents of which are hereby incorporated by reference.

The subject of the present invention is a device and a kit for positioning an implant for intervertebral fusion.

More specifically, the present invention relates to an instrument for positioning an implant during a spinal fusion surgical procedure, or an operation used to treat degenerative spinal conditions, such as stenosis of the spinal canal, using implants or grafts (cages) designed to join two or more adjacent vertebrae in order to stabilise the spine and reduce the pain caused by the condition.

As is known, there are several types of spinal fusion techniques, which differ according to the level at which the surgery is performed and the method used to access the spine.

For example, anterior interbody fusion (lumbar or cervical), posterior interbody fusion (lumbar or cervical) or even transforaminal interbody fusion procedures are known, in which the lumbar region of the spine is accessed through an incision in the patient's back.

The latter type of surgical procedure is of particular interest in the context of the present invention, which is nonetheless also applicable to the other types of procedures described briefly here (and others which are not).

There are numerous solutions for allowing the surgeon to perform such procedures, especially in light of the fact that there have been significant developments in spinal surgery in recent years.

Generally, such solutions all envisage the use of a device with a handle from which a rod protrudes, said rod having a gripping member at the end for the implant or cage to be fitted.

One distinctive feature of such devices is linked to the need to permit the rotation in situ of the implant once it has been positioned between the vertebrae, while also keeping it in the correct position during its insertion.

As such characteristics are mutually incompatible, in the prior art numerous solutions have been developed aimed at overcoming the problem by using specific coupling/uncoupling systems between the device and the implant. The prior art solutions include, for example, publication U.S. Pat. No. 8,579,904, filed by this same Applicant, which describes an instrument for positioning an implant for intervertebral fusion provided with a toothed clamp that can be coupled with a corresponding splined pin of the implant.

By closing the gripper, the device can be inserted (from the front or from the rear) without the risk of any accidental rotational movement and, once the implant has been inserted between the vertebrae, the implant can be temporarily released to change the angle of coupling with the device so that, after re-closing the gripper, the assembly can be rotated.

This solution, while actually giving the surgeon maximum freedom of positioning, introduces a non-trivial problem in the surgical procedure, in that the implant has to be released completely before being definitively positioned.

To overcome this problem, further devices have been placed on the market which are capable of allowing the rotation of the implant while it is still connected to the rod.

For example, document US2007/093850 describes a device in which the rod is divided into a main portion and an end portion rotatably coupled to one another at an elbow joint designed to facilitate the "guided" rotation of the implant (connected to the end portion), by means of specific control means.

While overcoming the inconveniences mentioned above, this solution is not very practical for the surgeon, and is mechanically complicated, in that the centre of rotation is much further away from the object to be rotated (i.e., the implant), which actually increases the operating area of the device. Similar considerations apply to the device described in document US2008/306409, in which the centre of rotation of the implant is again removed with respect to the implant connection pin and the system of rotation is complicated and expensive.

A further known solution is presented in document US2007/0225808, which describes a device in which:
 the end portion of the rod is defined by a hook able to translate between a retracted position and an extracted position, defining respective locking and releasing configurations of the implant;
 a toothed coupling system for controlling the rotation of the implant about a splined pin thereof.

This solution, which is excellent in terms of the combination of safety and versatility, is however extremely expensive and cumbersome, since the entire system for transmitting the rotational motion developed starting from the handle has to be housed in the space inside the rod.

The purpose of the present invention is therefore to provide a device and a kit for positioning an implant for intervertebral fusion that overcomes the drawbacks of the prior art described above.

In particular, the purpose of the present invention is to provide a device and a kit for positioning an implant for intervertebral fusion that are simple and at the same time efficient.

A further purpose of the present invention is to provide a device and a kit for positioning an implant for intervertebral fusion that are reliable and easy for the surgeon to handle.

Said purposes are achieved with a device for positioning an implant for intervertebral fusion having the characteristics of one or more of the appended claims from 1 to 14, and a kit for positioning an implant for intervertebral fusion having the characteristics of any one of the claims from 15 to 17.

In particular, the device comprises a handle, a rod protruding from said handle along a main direction of extension of the device, up to a free end and coupling means with an implant for intervertebral fusion operatively active at said free end.

According to one aspect of the present invention, the coupling means comprise an axial retention assembly provided with a gripper formed at said free end and selectively operable between a clamping and a releasing configuration, and an anti-rotational constraint assembly selectively movable between a locking position, in which it is arranged around said axial retention assembly and abuts said implant to prevent its rotation, and a disengagement position, in which it leaves the implant free to rotate in said gripper.

Advantageously, in this way the axial retention can be disengaged from the rotational constraint of the implant, to guarantee both ease of use and structural simplicity.

The presence of an axial retention gripper and of an "external" anti-rotational constraint assembly suitable to selectively block the rotation of the implant means that the number of components can be reduced to a minimum and, above all, eliminates the need for complicated transmissions, toothed wheels or threaded couplings.

Preferably, the gripper is defined by a pair of jaws facing one another to define a zone for receiving a rotation pin of said implant. Said grippers are movable towards and away from one another between said clamping and releasing configurations.

The jaws preferably have the shape of a hook with substantially smooth concavity facing towards the other jaw in order to delimit a seat to allow the rotation of said pin even in the clamping configuration.

Preferably, furthermore, the device comprises a manoeuvring element provided with at least a rotatable actuating body and configured to convert a rotation of said actuating body into a movement of the gripper.

In particular, the manoeuvring element is shaped so that:
a rotation of the actuating body in a first direction corresponds to a tightening movement of the gripper;
a rotation of the actuating body in a second direction corresponds to a releasing movement of the gripper.

Even more preferably, the gripper is defined by a pair of prongs at the end of the rod inserted in a tubular sleeve which is able to slide with respect to them in order to move between a first position, proximal to the handle, and a second position, distal to the handle.

More precisely, the prongs and the sleeve are shaped in such a way that a translation of the sleeve from the first to the second position causes a switching of the gripper from the release configuration to the clamping configuration, and vice versa.

Preferably, to move the sleeve, the actuating body of the manoeuvring element comprises a threaded nut axially constrained to said tubular sleeve and rotatably coupled to a threaded portion of the handle, so that a rotation of the threaded nut (or of the actuating body) corresponds to a translation of the tubular sleeve (and thus a movement of the gripper).

With reference to the anti-rotational constraint assembly, this preferably comprises at least an abutment element slidably associated with said rod and selectively movable between a position proximal to the handle and a position distal to the handle, corresponding, respectively, to the disengagement and locking positions.

Moreover, said assembly further comprises a pawl, in addition to and opposite the abutment element.

Said pawl is shaped so as to define an end stop for the rotation of the implant in at least one direction of rotation.

The presence of this pawl, on one side, and of the abutment element, on the other, means that in at least one predetermined angular position of the implant, the abutment element prevents the rotation of the implant in a first direction and the pawl prevents the rotation of the implant in a second direction.

Therefore, advantageously, this solution allows the surgeon to position the implant in a predetermined angular position, preferably corresponding to the position of insertion, in which the abutment element and the pawls are in the engagement configuration and, since they are arranged on both sides of the implant, they prevent the rotation thereof.

These and further characteristics, and the respective advantages, of a device and a kit for positioning an implant for intervertebral fusion will be more apparent from the description that follows of a preferred and non-exclusive embodiment represented solely by way of non-limiting example in the accompanying figures, wherein.

Figure 1:
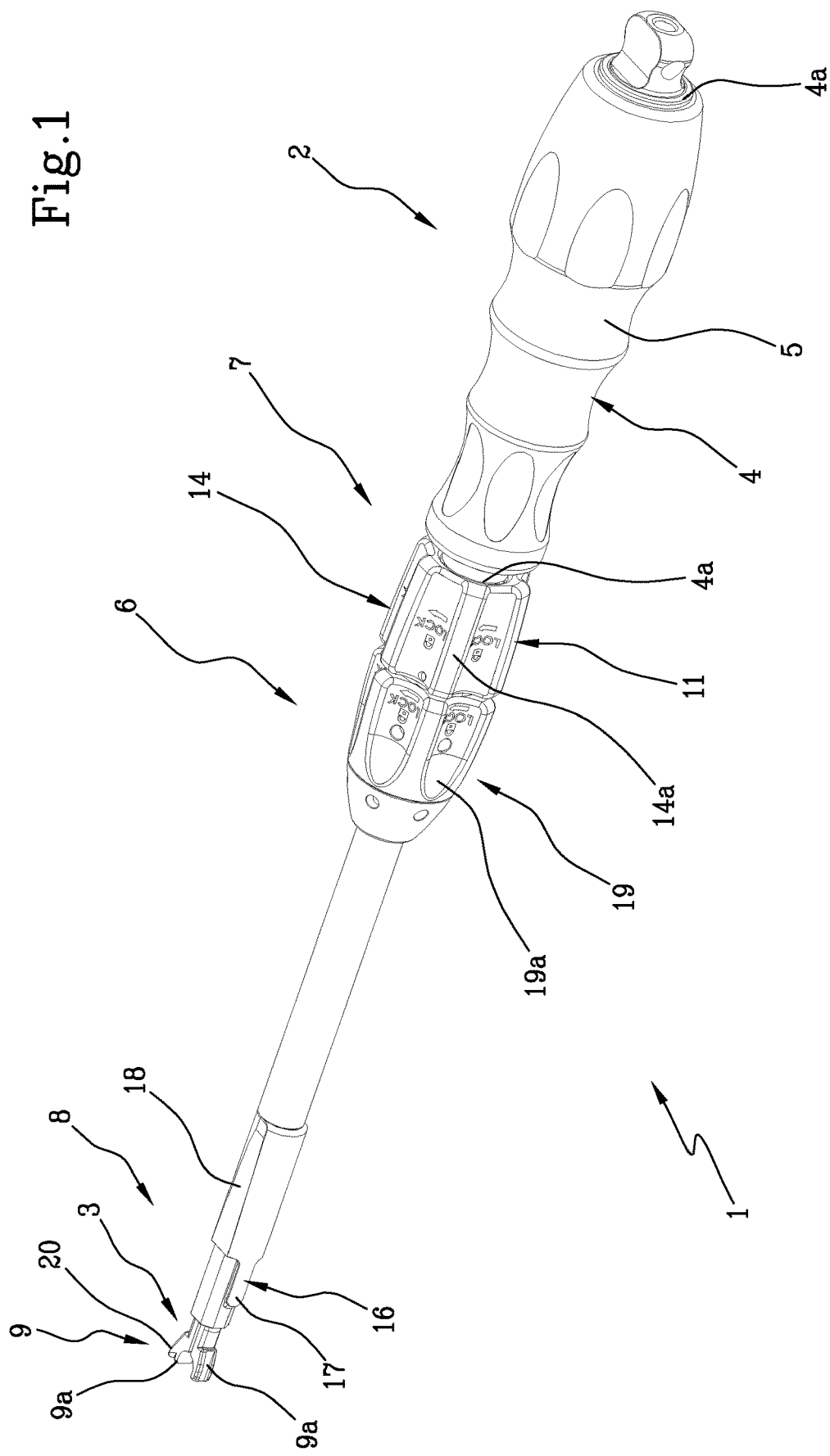
FIG. 1 shows a perspective view of a preferred embodiment of a device for positioning an implant for intervertebral fusion according to the present invention.
Figure 2:
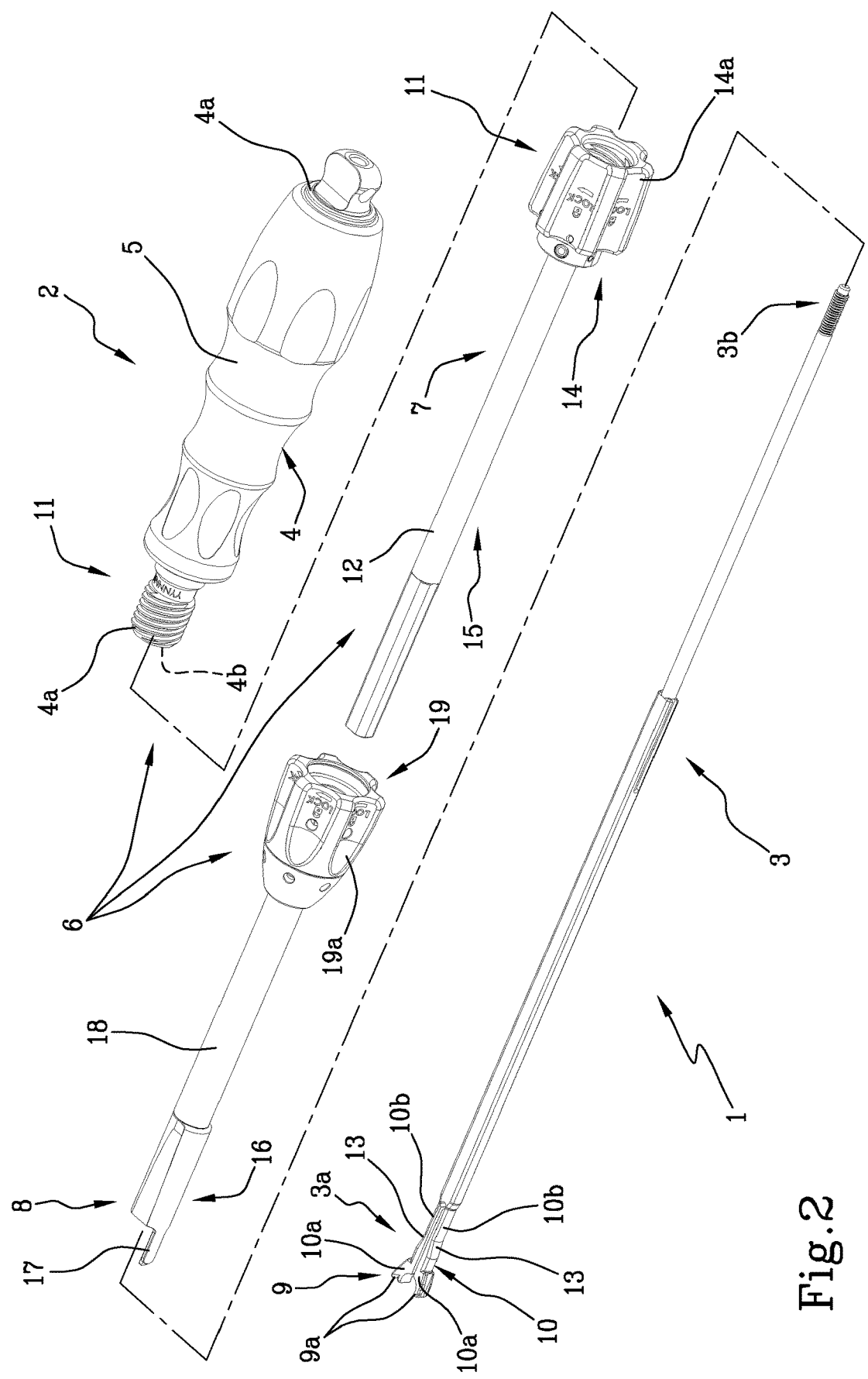
FIG. 2 shows an exploded view of the device shown in FIG. 1.
Figure 3:
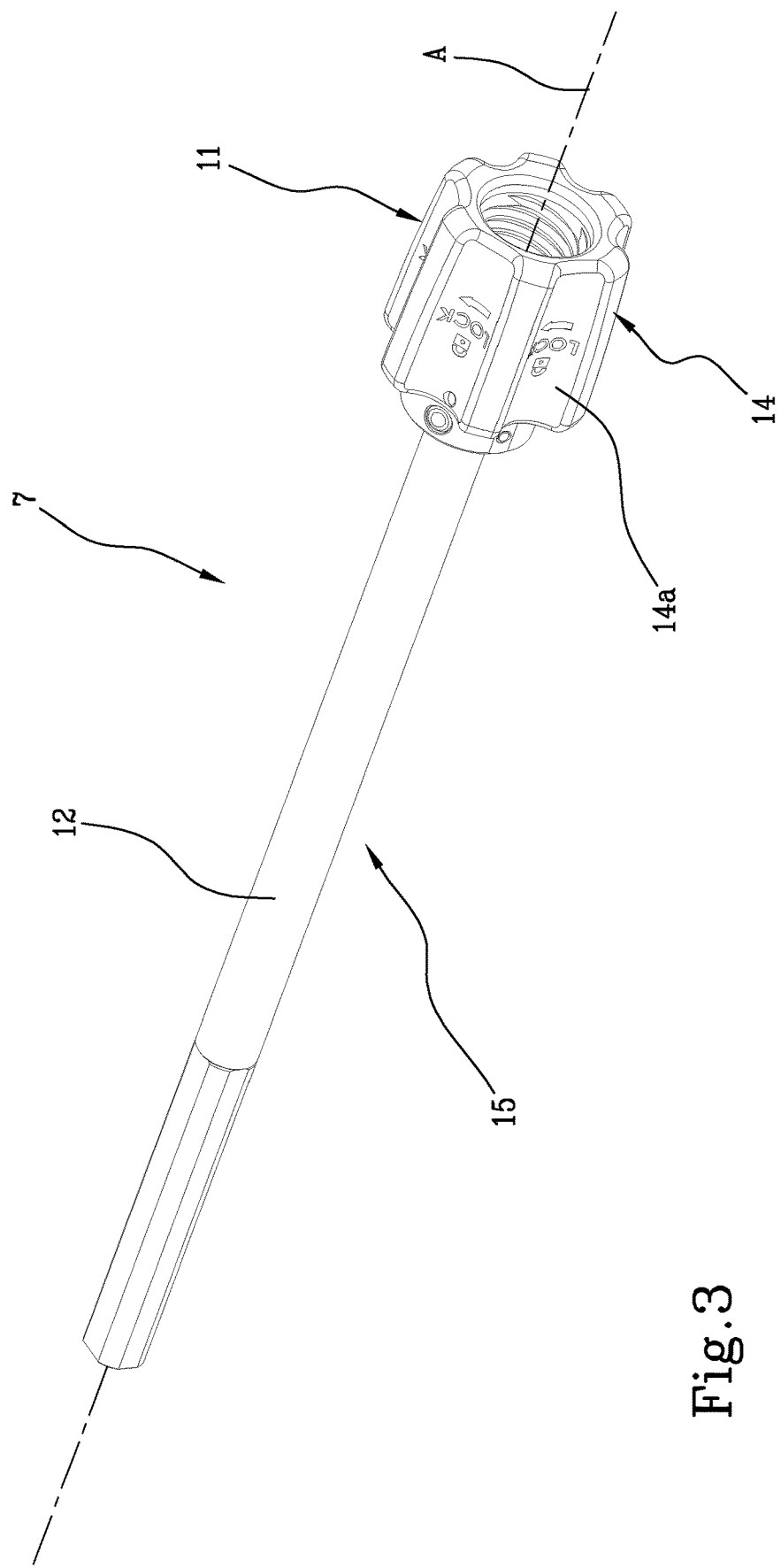
FIG. 3 shows a detailed perspective view of a first component of the device shown in FIG. 1.
Figure 4:
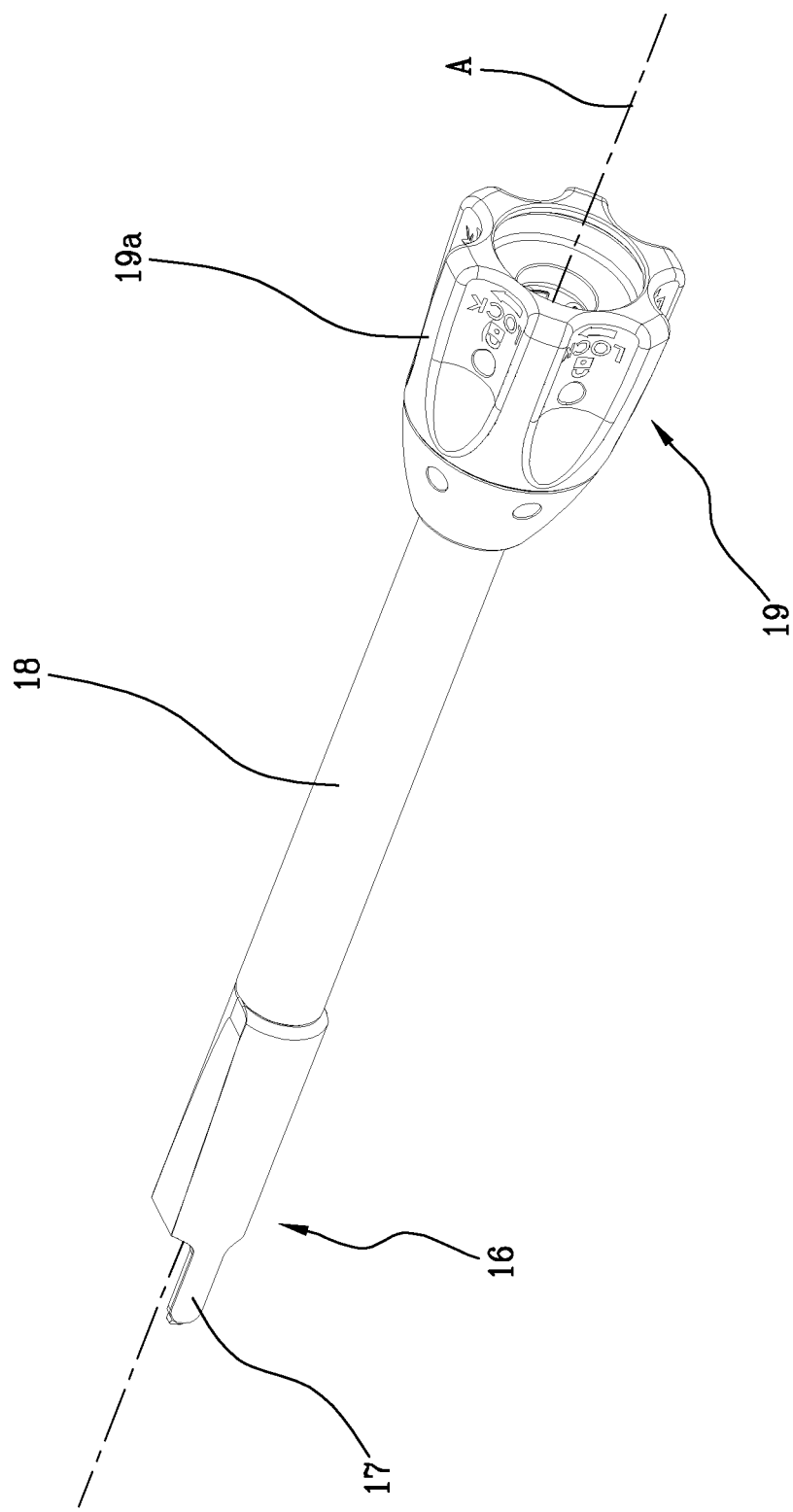
FIG. 4 shows a detailed perspective view of a second component of the device shown in FIG. 1.
Figure 5:
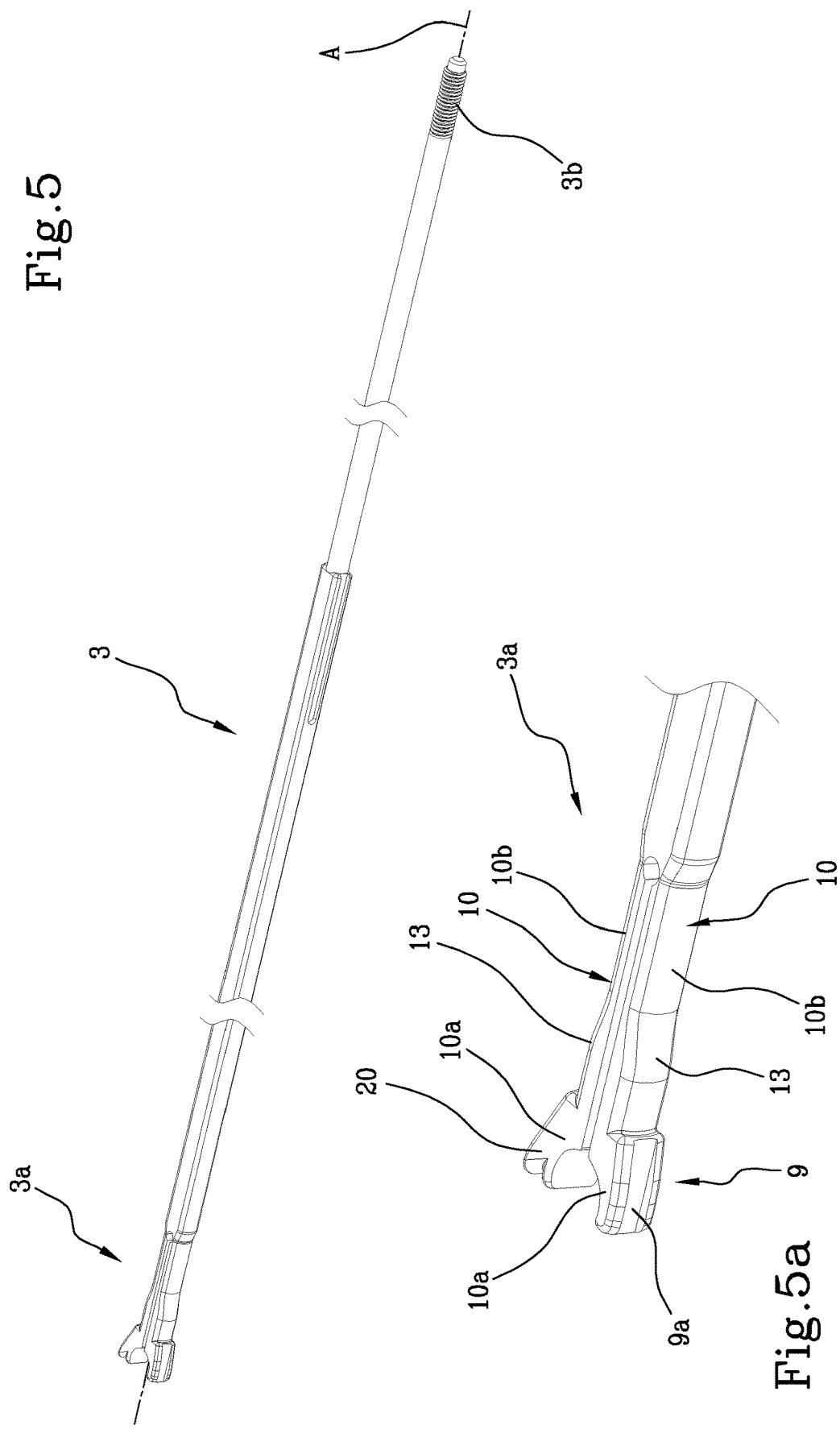
FIG. 5 shows a detailed perspective view and a detail of a third component of the device shown in FIG. 1.
Figure 6:
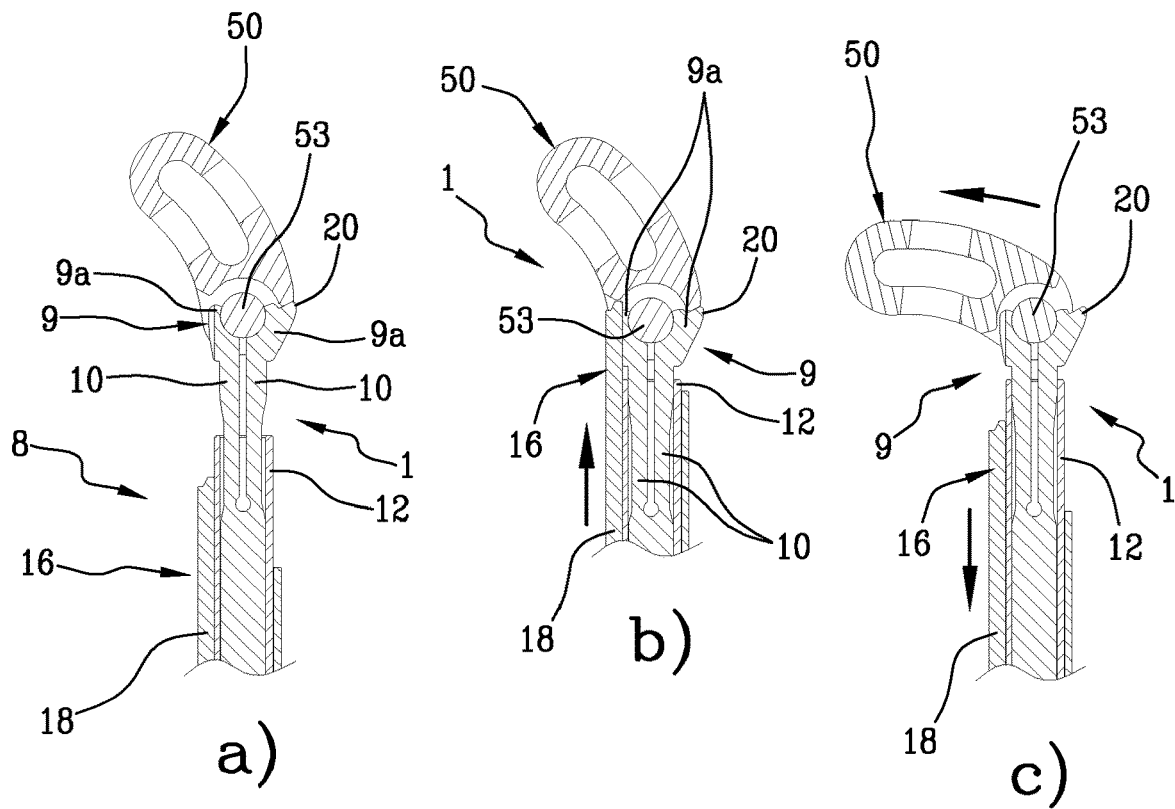
FIGS. 6a-6c show a sequence of operating positions of a kit for positioning an implant for intervertebral fusion according to the present invention.
Figure 7:
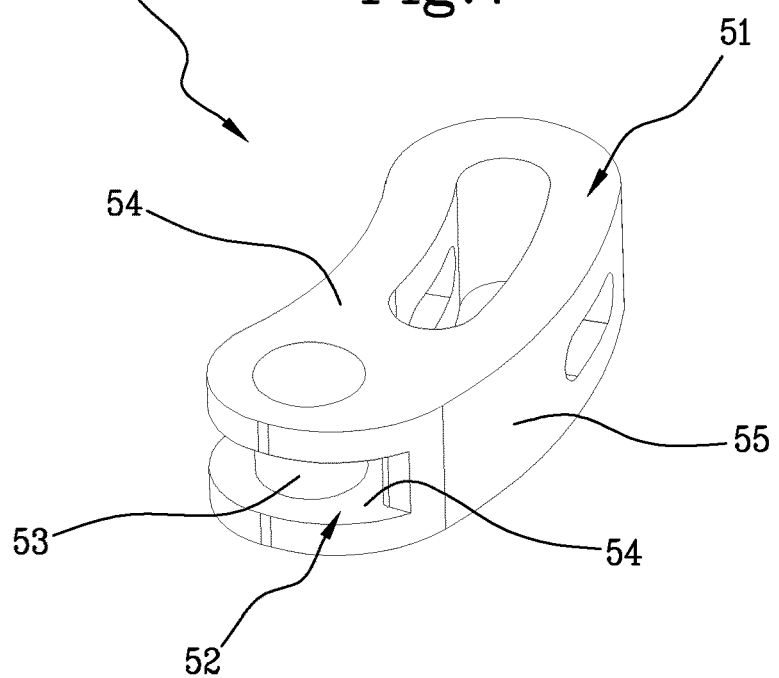
FIG. 7 shows a perspective view of an implant for intervertebral fusion that can be used with the device and the kit according to the present invention.

With reference to the accompanying Figures, numbers 1 and 100 indicate, respectively, a device and a kit for positioning an implant for intervertebral fusion according to the present invention.

The kit 100, or the assembly formed by the device 1 and an implant 50 (or cage) for intervertebral fusion, is specifically produced so as to permit intervertebral surgical procedures that comply with the most stringent requirements of modern minimally invasive surgery.

The device 1 and the implant 50 are both mainly designed for use in transforaminal cervical or lumbar intervertebral surgery, however, there is nothing to prevent the use of the same components and concepts for other types of surgery, for instance anterior interbody fusion (lumbar or cervical) or posterior interbody fusion (lumbar or cervical).

The implant 50 comprises a main body 51, preferably made of a biocompatible and radiotransparent material, such as PEEK, for example, or a similar material.

More precisely, the implant 50 comprises a portion 52 that can be coupled with the positioning device 1, preferably defined by at least one substantially cylindrical pin 53, defining an axis of rotation of the implant, as will be described in more detail below.

In detail, the implant 50 has an elongated shape, substantially a "kidney bean" shape, extending from the pin 53 along a curved path.

The pin 53 defines a spacer between two bases 54 extending according to the shape referred to above and delimiting a free space for receiving a cancellous bone graft or bone substitute.

Furthermore, there are at least two sides 55 that partially block the access from the side to the free space and define abutment elements that will be described in more detail later on.

As for the device 1, it comprises a handle 2 and a rod 3 protruding from the handle 2 and extending along a main direction "A" of the device up to a free end 3a.

The handle 2 is preferably defined by an elongated body 4 extending between two end portions 4a thereof. Said elongated body is preferably partially rounded, or ergonomically shaped, and is coated with a layer of non-slip material 5, for example rubber or a similar material.

The rod 3 extends from an end portion 4a of the handle 2 (or of the elongated body 4) away from the latter up to its free end 3a.

Preferably, the rod 3 is substantially rectilinear and extends entirely along the direction "A".

In the embodiment that is illustrated, the elongated body 4 of the handle 2 comprises a cavity 4b to house the rod 3.

Therefore, the rod 3 preferably has a portion housed in (and fixed to) the handle 2 and a portion protruding therefrom along the direction "A".

Thus, the rod 3 substantially extends between the free end 3a and an end 3b that is constrained to the handle 2 (or to the elongated body 4), preferably in correspondence with an end portion 4a of the elongated body 4 distal to said free end 3a.

In the embodiment that is illustrated, the coupling between the constrained end 3a of the rod 3 and the handle 2 is obtained by means of a shoulder and a threaded coupling.

Preferably, the device 1 further comprises coupling means 6 with the implant 50 operatively active at the free end 3a of the rod 3.

According to one aspect of the present invention, the coupling means 6 comprise an axial retention assembly 7 and an anti-rotational constraint assembly 8 which are separate but complementary.

The axial retention assembly 7 is preferably provided with a gripper 9 arranged at the free end 3a of the rod 3 and selectively operable between a clamping and a releasing configuration.

Said gripper 9 comprises a pair of jaws 9a (or arms) facing one another to define a zone for receiving the rotation pin 53 of said implant and movable towards and away from one another between said clamping and releasing configurations.

Preferably, the jaws 9a have the shape of a hook with their concavity "C" facing towards the other jaw 9a and have respective free ends which:

in the clamping configuration are arranged at a distance that is less than the diameter of the pin 53 of the implant 50;

in the releasing configuration are arranged at a distance that is more than (or equal to) the diameter 53 of the pin 50.

Preferably, the concavity of the jaws 9a has a substantially smooth surface in order to permit the rotation of said pin 53 even in the clamping configuration.

In other words, the pin 53 and the jaws 9a are shaped so that even in said clamping configuration the implant 50 is able to rotate with respect to the gripper 9 at least by a predetermined angle.

Therefore, the walls of the jaws 9a, or the concavities, do not define an anti-rotational coupling with the pin 53 of the implant.

It should thus be noted that the centre of rotation of the implant 50 is the actual pin 53 of the implant, which minimises the footprint area of the device during the operation.

In that respect, note that the sides 55 of the implant are spaced from the pin 53 so that each one defines a receiving window for the free end of the respective jaw 9a, thus enabling the rotation.

Preferably, with reference to the preferred embodiment, the gripper 9 is defined by the free end 3a of the rod 3.

In particular, the free end 3a of the rod 3 comprises a pair of prongs 10, parallel and adjacent to one another, elastically movable towards and away from each other.

In other words, the free end 3a of the rod 3 is fork shaped, with two fork arms defined by the prongs 10.

Each prong 10 thus extends between a connection portion 10a with a central body of the rod 3 and a free portion 10b, defining a respective jaw 9a.

Thus, the free portion 10b of the prong 10 is curved so as to define the hook shape of the jaw 9a.

In order to move the jaws 9a, or the prongs 10, towards and away from each other, the retention assembly 7 comprises a manoeuvring element 11 that can be selectively operated by the surgeon.

Said manoeuvring element 11 is thus associated with the gripper 9 and configured to switch it between the clamping configuration and the releasing configuration when operated by the surgeon.

Preferably, the manoeuvring element 11 comprises at least a rotatable actuating body 14 that can be used by the surgeon to impart the movement to the jaws 9a.

Said manoeuvring element 11 is configured to convert a rotation of said actuating body 14 into a movement of the gripper 9.

More precisely, a rotation of the actuating body 14 in a first direction corresponds to a clamping movement of the gripper, whereas a rotation of the actuating body 14 in a second direction, opposite to the first, corresponds to a releasing movement of the gripper.

Preferably, the actuating body 14 is associated with an actuating member 15 operatively active on said gripper 9 to close and/or open the jaws 9.

In that respect, preferably, the manoeuvring element 11 comprises a tubular sleeve 12 partially containing and slidably associated with said prongs 10.

In particular, the sleeve 12 is dimensioned to fit around the connection portion 10a of the prongs 10, so that the free portions 10b (i.e., the jaws 9a) protrude in any axial position of said sleeve 12.

Said sleeve 12 at least partially defines said actuating member 15.

The sleeve 12 is thus slidably movable along the prongs 10 (thus along the rod 3) between a first position, proximal to the handle 2 and a second position, distal to the handle 2.

The prongs 10 and the sleeve 12 are shaped in such a way that a translation of the sleeve 12 from the first to the second position corresponds to a switching of the gripper from the release configuration to the clamping configuration, and vice versa.

In that respect, at least one of the prongs 10 (preferably both) comprises a widened, or flared portion 13, arranged in correspondence with the connection portion 10b.

The widened portion 13 is engageable by the tubular sleeve 12 as it slides from the first to the second position (or at least in said second position) to move the prongs 10, and thus the jaws 9a, towards each other.

In other words, the prongs 10 have respective inclined planes (the widened portions 13) which, once engaged by the longitudinal movement (along the direction "A") of the sleeve 12, impart a transverse movement to said prongs 10 so that they move towards each other.

Thus, the prongs 10 and the sleeve 12 are shaped so as to exploit the principle of the inclined plane.

Therefore, the manoeuvring element 11 is shaped in such a way that a rotation of the rotatable actuating body 14 corresponds to a translation of the sleeve 12 along the direction "A".

According to the preferred embodiment, the actuating body 14 comprises a threaded nut 14a axially constrained to the tubular sleeve 12 and rotatably coupled to a threaded portion of the handle 2. In this way, a rotation of the threaded nut 14 corresponds to a translation of the tubular sleeve 12.

Alternatively, however, the actuating body could be associated with the sleeve by means of kinematic mechanisms or other connection systems, such as a rack and pinion, ratchet or other known system.

Thus, structurally, the handle 2 is a hollow body into which the rod 3 is inserted and fixed. The manoeuvring element 11, preferably defined by a threaded nut 14*a* coupled to the handle and to a sleeve 12, is fitted on the protruding portion of the rod 3.

In that regard, note that the rod can be detached from the handle 2 by uncoupling its constrained end 3*b* and can be replaced, for example with further and different types of rods (e.g. with toothed gripper).

The anti-rotational constraint assembly 8 is, in turn, selectively switchable (i.e., movable) between a locking position and a disengagement position.

In the locking position, the anti-rotational constraint assembly 8 is at least partially arranged around the axial retaining assembly 7 and abuts the implant 50 to prevent its rotation in at least one direction of rotation, preferably in both.

In the disengagement position, the anti-rotational constraint assembly 8 is removed from a footprint area of the implant 50 and leaves it free to rotate in the gripper 9.

Thus, preferably, the anti-rotational constraint assembly 8 comprises at least an abutment element 16 slidably associated with the rod 3 and selectively movable between a position proximal to the handle 2 and a position distal to the handle 2, corresponding, respectively, to the disengagement and locking positions.

In the position distal to the handle 2, the abutment element 16 is next to the gripper 9 and contrasts the implant 50 so as to prevent the rotation thereof.

More precisely, the abutment element 16, in its distal position, corresponding to the locking position, abuts a side 55 of the implant 50.

Preferably, the abutment element 16 is at least partially defined by a rigid tab 17 extending along the main direction "A" and next to the rod 3.

Said tab 17, in the position distal to the handle 2, is next to the gripper 9 and, in use, abuts the implant 50 (on the side 54) to prevent the rotation thereof in at least one direction.

According to the preferred embodiment, the tab 17 is arranged along the tubular sleeve 12.

More precisely, the abutment element 16 comprises a tubular body 18 fitted on the sleeve 12 of the retention assembly 7 and slidable with respect to the latter between said distal and proximal positions.

The tab 17 protrudes longitudinally from said tubular sleeve 18, and in particular from an end portion thereof distal to the handle 2.

Advantageously, in this way when the tubular body 18 substantially reaches an end of the sleeve 12, or abuts the jaws 9*a*, the tab 17 continues next to one of the jaws 9*a* and beyond it, until abutting the side 55 of the implant 50.

Preferably, the anti-rotational constraint assembly 8 further comprises a clamping system 19 of the tubular body 18 and/or of the tab 17, configured to allow the surgeon to lock the axial position thereof between the distal position and the proximal position.

According to the preferred embodiment, the clamping system 19 comprises a clamping nut 19*a*, selectively switchable between a locked condition, in which it constrains the tubular body 18 and/or the tab 17 to the sleeve 12, and a loose condition, in which it allows a translation of the tubular body 18 and/or of the tab 17 along the sleeve 12.

More precisely, the clamping nut 19*a* is coupled to a clamp and is configured to switch it between a loose condition, in which it allows the tubular body 18 to slide on the sleeve, and a locked condition in which it grips the sleeve 12 to prevent it from sliding.

Advantageously, in this way the abutment element 16 can be moved integrally with the sleeve 12 or separately from it according to the surgeon's needs.

Preferably, moreover, the anti-rotational constraint assembly 8 comprises a pawl 20, in addition to and opposite the abutment element 16.

Said pawl 20 is shaped so as to define an end stop for the rotation of the implant 50 in at least one direction of rotation.

Said pawl 20 thus determines the angular position corresponding to the position of insertion of the implant.

The abutment element 16 (or the tab 17) is thus shaped to abut the implant 50 at least in said angular position, so as to prevent the rotation thereof.

Thus, the abutment element 16 and the pawl 20 are both arranged next to a respective jaw 9*a* of the gripper 9 so that, in at least a previously defined angular position of the implant 50, they prevent the rotation of said implant 50 in both directions of rotation.

Therefore, at least in the position of insertion of the implant 50, both the abutment element 16 and the pawl 20 abut the sides 54 of the implant 50, which therefore define abutment shoulders for the anti-rotational constraint assembly 8 of the device 1.

Preferably, said pawl 20 is made in one piece with one of the jaws 9*a* of the gripper 9.

This is particularly advantageous in view of the fact that during the operation the surgeon needs to rotate the implant 50 in a single direction, so that it suffices to allow freedom of movement in that direction to guarantee maximum manageability and precision for the user.

The invention achieves the purposes described previously and brings some important advantages.

The presence of a retaining assembly detached from the anti-rotational constraint assembly gives the surgeon maximum freedom of action and, at the same time, maintains a high standard of safety and degree of precision of the operation.

Moreover, the availability of a closable gripper in which the implant can rotate freely makes the structure of the device very simple and at the same time reliable.

Furthermore, the fact that the implant anchoring pin is also the centre of rotation of the implant greatly facilitates the surgeon's work, and also reduces the operating space required (which makes the operation even less invasive).

The invention claimed is:

1. A device for positioning an implant for intervertebral fusion, comprising:
    a handle;
    a rod protruding from the handle along a main direction of extension of the device up to a free end comprising a pair of prongs parallel and adjacent to each other, elastically movable towards and away from each other;
    a coupler which couples with an implant for intervertebral fusion operatively active at the free end;
    wherein said coupler comprises:
    an axial retention assembly provided with a gripper arranged at said free end of the rod and selectively operable between a clamping and a releasing configuration, and
    an anti-rotational constraint assembly selectively movable between a locking position, in which the anti-rotational constraint assembly is arranged around said axial retention assembly and abuts said implant to prevent rotation of the implant, and a disengagement position, in which the anti-rotational constraint assembly leaves the implant free to rotate in the gripper; and wherein the axial retention assembly and the anti-rotational constraint assembly are structurally different and complementary, wherein the axial retention assembly comprises a maneuvering element associated with the gripper and is configured to toggle the gripper between the clamping configuration and the releasing configuration when operated by a user, wherein the maneuvering element comprises a tubular sleeve partially containing and slidably associated with said prongs to move between a first position, next to the handle, and a second position, distal to the handle, and wherein the anti-rotational constraint assembly comprises at least an abutment element slidably associated with said rod and selectively movable between a position next to the handle and a position distal to the handle, corresponding respectively to the position of disengagement and the locking position of the anti-rotational constraint assembly, and said abutment element comprises a tubular body fitted on said tubular sleeve of the axial retention assembly that is slidable with respect thereto between said distal and proximal positions.

2. The device according to claim 1, wherein the gripper comprises a pair of jaws facing one another to define a zone for receiving a rotation pin of said implant and movable towards and away from one another between said clamping and releasing configurations.

3. The device according to claim 2, wherein the jaws have the shape of a hook with substantially smooth concavity facing towards the other jaw in order to allow the rotation of the pin in the gripper even in the clamping configuration.

4. The device according to claim 2, wherein each of said prongs extends between a connection portion with a body of the rod and a free portion defining a respective jaw of the gripper.

5. A device according to claim 1, wherein the maneuvering element comprises at least a rotatable actuating body and is configured to convert a rotation of said actuating body in a first direction into a tightening movement of the gripper and a rotation of the actuating body in a second direction into a release movement of the gripper.

6. The device according to claim 5, wherein each of said prongs of the rod extends between a connection portion with a body of the rod and a free portion defining a respective jaw of the gripper.

7. A device according to claim 6, said prongs and said sleeve of the maneuvering element is shaped in a way that upon a translation of the sleeve from the first to the second position, the gripper switches from the release to the clamping configuration, and vice versa.

8. The device according to claim 7, wherein each of the prongs comprises an enlarged portion, engageable by said tubular sleeve, at least in said second-position, in order to move them towards each other.

9. The device according to claim 5, wherein the actuating body of the maneuvering element comprises a threaded nut constrained to said tubular sleeve and rotatably coupled to a threaded portion of the handle, so that a rotation of the threaded nut corresponds to a translation of the tubular sleeve.

10. The device according to claim 1, wherein the abutment element is at least partly defined by a rigid tab which in said position distal to the handle is next to the gripper and, when in use, the abutment element abuts said implant in order to prevent rotation of the implant in at least one direction.

11. The device according to claim 10, wherein the anti-rotational constraint assembly comprises a pawl, in addition to and opposite the abutment element, shaped so as to define an end stop for the rotation of the implant in at least one direction of rotation.

12. The device according to claim 11, wherein the abutment element and the pawl are each next to a respective jaw of the gripper so that, in at least one predetermined angular position of the implant, the abutment element prevents the rotation of the implant in a first direction and the pawl prevents the rotation of the implant in second direction, opposite to the first.

13. The device according to claim 12, wherein the pawl is made in one piece with a jaw of said gripper.

14. The device according to claim 1, wherein said anti-rotational constraint assembly further comprising a clamping nut selectively switchable between a locked condition, in which the clamping nut constrains the tubular body to the sleeve, and a loose condition, in which the clamping nut allows a translation of the tubular body along the sleeve.

15. The device according to claim 5, wherein said anti-rotational constraint assembly further comprising a clamping nut selectively switchable between a locked condition, in which the clamping nut constrains the tubular body to the sleeve, and a loose condition, in which the clamping nut allows a translation of the tubular body along the sleeve.

16. A kit for positioning an implant for intervertebral fusion, comprising:

a handle;

a rod protruding from the handle along a main direction of extension of the device up to a free end comprising a pair of prongs parallel and adjacent to each other, elastically movable towards and away from each other;

a coupler which couples with an implant for intervertebral fusion operatively active at the free end;

wherein said coupler comprises:

an axial retention assembly provided with a gripper arranged at said free end of the rod and selectively operable between a clamping and a releasing configuration, and an anti-rotational constraint assembly selectively movable between a locking position, in which the anti-rotational constraint assembly is arranged around said axial retention assembly and abuts said implant to prevent rotation of the implant, and a disengagement position, in which the anti-rotational constraint assembly leaves the implant free to rotate in the gripper;

wherein the axial retention assembly and the anti-rotational constraint assembly are structurally different and complementary;

wherein the axial retention assembly comprises a maneuvering element associated with the gripper and is configured to toggle the gripper between the clamping configuration and the releasing configuration when operated by a user, wherein the maneuvering element comprises a tubular sleeve partially containing and slidably associated with said prongs to move between a first position, next to the handle, and a second position, distal to the handle, wherein the anti-rotational constraint assembly comprises at least an abutment element slidably associated with said rod and selectively movable between a position next to the handle and a position distal to the handle, corresponding respectively to the position of disengagement and the locking position of the anti-rotational constraint assembly, and said abutment element comprises a tubular body fitted on said tubular sleeve of the axial retention assembly that is slidable with respect thereto between said distal and proximal positions, and at least one implant for intervertebral fusion provided with a portion that can be coupled with the rod.

17. The kit according to claim 16, wherein the portion that can be coupled comprises at least one substantially cylindrical pin that can be housed in the gripper and a pair of receiving seats for a free end of the jaws.

18. The kit according to claim 17, wherein the implant further comprises a pair of abutment shoulders for the anti-rotational constraint assembly of the device in the locking position.

\* \* \* \* \*